(12) United States Patent
Lin et al.

(10) Patent No.: US 9,763,431 B2
(45) Date of Patent: Sep. 19, 2017

(54) **TILAPIA (*OREOCHROMIS NILOTICUS*) MYOSIN LIGHT CHAIN 3 PROMOTER**

(71) Applicants: ACADEMIA SINICA, Taipei (TW); Yu-Ho Lin, Kaohsiung (TW)

(72) Inventors: Yu-Ho Lin, Kaohsiung (TW); Jyh-Yih Chen, Ilan (TW)

(73) Assignees: ACADEMIA SINICA, Taipei (TW); Yu-Ho Lin, Kaohsiung (TW)

( * ) Notice: Subject to any disclaimer, the term of this patent is extended or adjusted under 35 U.S.C. 154(b) by 13 days.

(21) Appl. No.: 14/920,497

(22) Filed: Oct. 22, 2015

(65) Prior Publication Data

US 2016/0113252 A1    Apr. 28, 2016

Related U.S. Application Data

(60) Provisional application No. 62/067,298, filed on Oct. 22, 2014.

(51) Int. Cl.
*A01K 67/027*    (2006.01)
*C12N 15/85*    (2006.01)
*C07K 14/46*    (2006.01)

(52) U.S. Cl.
CPC ........ *A01K 67/0275* (2013.01); *C07K 14/461* (2013.01); *C12N 15/8509* (2013.01); *A01K 2217/052* (2013.01); *A01K 2217/206* (2013.01); *A01K 2227/40* (2013.01); *A01K 2267/02* (2013.01); *A01K 2267/0393* (2013.01); *C12N 2830/008* (2013.01)

(58) Field of Classification Search
CPC .......... A01K 67/0275; A01K 2217/206; A01K 2227/40; A61K 49/0013; C07K 2319/61; C12N 5/8509; C12N 2830/008
See application file for complete search history.

(56) References Cited

PUBLICATIONS

Oliveira and Wright, Chromosome Res. 6(3):205-211, 1998.*
Katagiri et al, Animal Genetics 32(4):200-204, 2001.*
Soler et al, BMC Genomics 11: 636, pp. 1-8, 2010.*

* cited by examiner

*Primary Examiner* — Kevin Hill
(74) *Attorney, Agent, or Firm* — Birch, Stewart, Kolasch & Birch, LLP

(57) ABSTRACT

The preset invention relates to a promoter to target a fluorescent protein to the muscles of fish, such as *A. nigrofasciatus*, for ornamental purposes, which is a Mlc3 (myosin, light polypeptide 3, skeletal muscle) promoter. The Mlc3 promoter has the nucleotides of tilapia (*Oreochromis niloticus*) myosin light chain 3 (Mlc3) promoter region, which is potential to be a tilapia Mlc3 promoter to enhance protein expression in muscle of fish, particularly for the generation of ornamental fish.

6 Claims, 7 Drawing Sheets

```
TTCTCTTTTTCTTCCTCTGTGGGACCATTAGCTCATCTAATCCAGTCTTTTCCATATAAGGCTCATGCTGAAAACCAAGCAGCAACACAA
TGCCATCTCTCTTTTTTAAGCTCCCTGCCAGAGCTCCTTTATGACCCAAGGCCAGCTTGGTAGAAGGAGGTGGTGAAGGGGGAGGTGGC
TACTGTACCAGAGAGTCTTGAGATCCCAGTCTCCGCAGAGCAAACGCAGCGTAGGAGAAACTCAACACCGCCAGTGGGAATGAGAGT
AAAAATAGAGCTCATCTGTCCAGGAGGGGAGTGGTCTCCAAGAGCATGTGCTCCACTGTGGTTCACGCGCTCCTACAAGTGTCCTCCA
ACGTGTCCGTTCTGATGCTCAGCAGCTGATTGCTTTGTGTTACATAGACGATGACAAGTTAGGCAGCCTAGCAGCACTATAAGTGAATT
ATCTAATCGTGTGTGCTGTCACAATATAAATGCACTGACCTTTTCTTATAGATTTGTCTTTCCTTCCTTTTGGATCTACTTTAGAGAAAA
AAATTCTTCTATTTTAACAATCGTATATTGTTAAAATGTACTTAACCAAAAGGCCAAAAAATGTTTATGGAAATCTGCTGTATTCTTAC
AACTGGTTGTACTTAAGGAGGATCACAGGCATGTAGTAATGTGCAAAAGTCTTGTTCCATCCCTCATTTCTTGGTGTTTAAGGCAAAAA
CAGAGTTTGTACAATTCTGTCAAGCTTGAAAGTCAATATTTGGTGTGACCACCTTTATTCTTCAGCACAGTCCGAACTCTCTTAGGCAG
CTTTCTTGTTATTTTTTAAGTTGTCTTCAGGAATAGTTCTCCAGGCTTCTTGAAGGACATTCAGAGCTCTTCTTTGGATGTTTAAGGACA
GGACTTTTAAATCTTGTCCATCTGCAGTTGATTTTTCAGGCCTGACATTTCTGCTTTGGCCCTCGACTCCAGTTTCCTCAAATTTTTTAAT
TTTGAGGAAACTGCAGTGCATATGCATATGCACACCATATGCACTGGAGACCTATTGCTCAAGACCAACTGACGGCAAGGAAGTCTCG
CTCATTGGAAGCAAAGTATTAACAATGACTTTTGCACAGTACTGTAGCTGGTATTTATACATAATTAGCATGATATTTTTCATTGATAA
GTTTATATTTCATTACACACACGCGCACGCAGGCATATATAGTCTCCCTCACCTAAACCAATCTGCCCTGAACCTTCTACAACACTCAG
TGTTAACACACAGGGATCACTGCTTCTAGGCTGTTACCCACATGGAGTCACATGTATGTGACAGCAGAGATGAGCATATATTTAACCTA
AAGCATGAAAAAAAACAAACCCAAACAGATTTCTTCTATGAAATTCACAGCTTTTTAAATTTTCAGCAAATTTTATATTTGAAATAATA
GTTTGTATCAACGGTACTGTCAAGTTGACAAGTAGACTTTCCTAAAAACAATACTATACCAGAAAGACTGTACTGACAATACAGGCCC
TGAAGCAGAAACCAAACCAGCAATAAACAAACCAATGAACATGACTATAAAATGACCTGTGAACACCAGAGCCTCCTTGTGTTTGGA
CCTATGGGTTGTTCCAAATAGAAAAAGAACTGCCAGAGGAACTGAAAAACCTAAATTAAGGATGGAAAAAGGATACAAGAAGACTGG
CGACCGACAGAAAGTCAGTCGAAGCACAGCTGCAGCAATAATCGTGCTAACCAGCGAACTGGCCTCCTAAAATGACACCATGGGCAGT
GCATTACTTGCACAGTCTAGCTCTGAGAAAGCTGGCGCTTCAGATTTGGCACAGGGTTTATAAATGGAAATGGCTCACAACACATAGC
ATAATGAGATCCTCTATGGACGGCACCCTAAGCGAAAAAACACTGCTGGCTCTTTAACGGAAAACTCTATGATCGAATTTTGCTAAAG
AATTCCAAAAGAAGGCTTATGAAAGTTGGGCGCATGCGGTCCACAGACGATGTCCATGTGAAAGATTTTGGGAAGACTGGTAGATTGT
GTATATACCAAAATACTGGTTGACAGGATGGCTCCCAGTCTGCAGAGGCCTAACAGAACAATGAGGAAACTGCCAGAATCACACTAC
AACCTGCCCTAGTATGTTGTCAGACTTGAATCCAATAATCACCTTTTTAAAGAGAAAAGCAGAGCAGCTGAAATCAAAGAATATCAGG
AAACTGTCAATACTGGCATCCCTCCAAACAGACAGCAATGAATAAATTATTTAAAAAACATGAAAGATTCGTATGAATATGACAGCCT
CTAACCAATCAAAGACTCCTATTATCTCTATTTTCCCTGTCTTGTCTCTATTTCTGCCTCCTTTTCTCAATAGTTTTTAGTTCTTTGTGCCT
GTTTCATGTAGCTGCTATGATGCTATATTACCTACTTGCCAACTGTTTACTTTTAGGGTCTGGTCACTATCTCCTACCTTCATTTGTGGTT
CTGCCCTGTGATACCAAACTAATTATGTAATTCGAACCAAGAGTCTAATTCTATCCGAAAAACTTACGTTTTAAAAATTTCTGCAACC
CTGAACTGATTGGATTGGATGGACGGATGGATGGATGGATGGATGGATGGATGGATGGATGGATGGATGGATGGATGGATGGATGGA
CAGACAGACGGATGTCAAACAACATATAAAGCCAATGGGTAAGTCATTAAGAAAAGATCTGTGGTCACCATGACACAACTTAGAGTC
GGGAGGATGGATGGATTCAATTAGATTTATTATTTGTCCTTTCAGAAATTTGTGCCTCGGGGCGACTGTCAGACAAATAACCACA
ACAACAATATCACAGTTACAGAGATAAAAGACATCTGTTTCATCCCACATCATAACAAATATCACCTGGATTGTTCACCAGAGTTGTA
CAAGGTATAAACAACCTTGGGGTGCGAGGTCCTCACAAAGCTGGTGTACTGTCTTGACTATGATGACTGTGTGTTACGTCCCTGTGAAT
GTCTCGCCCCTGTCCCATCACTCATGACTCCCAAAGCTGGCACACACTATGTTGTTGCTGACCTCTTACTGCCCATGTTTACAAGCCTAC
TGAGTTTGTTCTTATAAACCACGGAGAGTGAAAACACCAGACAATAAAAGAAAAAGTTAAAATGCTTTCTACAGATAAACGATTAAAA
AGCATCTATGAATCTAAACTGTTGGGTAATAATTGTATATGAGGATTAGTTACTATTACTTACATAAAGTAAGAATAACCTTGTTGCTT
TTGAAATTGTGATTTGTAATAGGTGGGCTATAAAATAACTTGAAAAATAAAACTGCACTTGGAGAATCAGAGGTAATGATATACTATAA
AGTCAATAAAATGCAAAGTGCAGAGAATTTTTTCCAGTTTTTTAAATTAAGTTTGTTACATCAAACAATGTATCAAGAAATTCATTTAT
TAAGATTAAAGCTTATTGCATTAAACAAAGTTTCTTTCTGCATCGCTGTCAGCACCATGGAGAGCTCTGCTGAAGATGGAAATGCCAAT
GAAATTGACTTTTAAAAACGTCATTTATTGTGCTATGAATGTAGTTCTTAGTAACATAACCTACATTATGTAAGTTTAACTTTCCTCCAG
TGTATTTGCCTATTTATTAATGGACAAACTGATCAGTTTTTATGTCAGCAAATCTGCACATTATGAATTTATTTGTTACTT
GTCCTATTCTGAGGGTAGCGCTGTGAGGACAGATCTTTTTAAGGTCTTTAGAATTGTTATAAAACCTGTTGTTTTCAGGTTATCTGCCGC
TCAGTGTCAATGCTTTTAACACATGCCTGAATGGAGTGAACTTTTCAAATGATTTTTCCCCCTCTTCTGTTATTTAACCATAAGAGGAGG
AGCAGTGGGGCTGTTTAAAAATACCACCCTGTAAATGAGCTCCTCGCACCTGGAGCCCTCCTCAAGTGAGCCTCAAGGAAGCTGAGTT
TTCTGCATTTTCACTCACCAGCTGTACATCTCTTTCCAGAGGAGAAGTCTAAGTGTCAATGCTGCCGAAAGCATTTTGGTTGAAATT
GTAATGCATTCACAGACTCTTTGAAATCTTGCGACCGTTCTTTCAGCCTTCTAAAAATAGCCCTGTCCCCTTCTAAAGGCTACTCCCAC
TGCTCCGAGGGCGTACAGCTCTCCTTTCCATTTGCCCTAAGAAAGTTAAAGATGTTCCAATGTGTCATCTGATCTGCCCATTAGCATAT
GTGACATCACATGCCCGGAATAAATAAGAGGGGTGCTTTGACCATGGCTAAGGACCACACTGTCTTGGGACTTCAGCTTCTCATCTCCT
CCAGCTCCTGCTCTCCAAAATGGTGTGTACGAACTTCTGTTTTGGACGTTGGGCATTGCTGATGGAGTTACCTTTTTTTTCCTT
TTAATTGGTTTGGATATCAGCTCGATAATGACCCCAAAACTGAGACTTTTGCTAGTGAGGCAAAATGAAGACTAGCACCCAGGACTAG
AGTCTTGGAATGCATTCACATGTATATGTTAATGTCTAAAAAGGCTTATATTCTAATGCAAAGAGGCCGTTTTAGAGTTTCAGCATCC
ATCATTTGTTCAGAACCCTTTTGGACAGTTACATAAGCTGGATATACTCATTTTGTTTTTCTTTATTTCTCTGTTTTCTGTGTGTTTGTGTA
TTTGTTAATGTGTGTTTTTAAATGTGACAGCTGAGTTCACACCGGACCAGATTGAGGGTAAGTGAAGAAAAGGAAAAAAAAGAGATTT
TGCCTCATATGTGAAGGCACCAACCTCTCAGTCAGTGTGCTGGTAGGCATTTACGTCTAACTTTTGCAACTGTCACACGAAACAAACTC
TCAGAGTAGCTCCAGACTTACTTAGATGAACTTTTAATCTGATTAAAGTGCTAGAAAAGTGGAAGCAGAGGATGAATAGCGCCATGCC
ATGCCATTCTACCAACTTCTCCAGCTGTCGGGAAAGATTTCAGACATGTCTATTCTCAGCTTGTCTTGCGAGTCCCCATGGTCCTTATTC
AGAAGGGGCATTAATCCTTAGGTCAGGGTTTAAGATGCAGTGCTGGTGGCATCAGCTTACACAAGAATCTGAATCACCCCATACCTTTT
TTGTTTAACTGCCGAAAGACATGTCCTCTATAAACATGCCCTATGGGATATATTAGGGGTCCCCATTTGGACATGGATACTTTTGTGTA
GTTAAAACTCTTCCAGTTGTGTATCCTAGACTTGCAGGCAAACCTTTAACGAGTTTTCAATCAGGCTTATTTGTTTAGTGCTGCTTCTAC
ACATTCTGGTACAAGCTATACTATATGTCTAACATTAAGTTCCTTTCCAAGCTCACGGTGTTAATTACGGCCCAGTCAGCATTCTTGGGTTT
GACTGCACGGAGGGCCATGTCGCTATGTCTCTAAATGGCCTGCGTTTCTCTGTCAGGGTGTATCAGTTTGCTCGCAATGTTGCTGTAAA
TGCAAGTGGAGGCAGGAATGTAGAAGGACGGGGTGGGTCGAGTGTGGTGGAAGGGTACAACTGCTGTTCAGAAGCCACACGAACACA
TTAATCTGTCAAAAAGGTCACTTTGAGTTCCTGGTGGGATTCACAGACATAGCCAACCATTGTCTGGGCCCCCAGTTGGTGCCTTCCTC
TTCACAGCTGTCCCTCTCAATTAGCTGAGAACAATGACAGAATTATGTGCTTTTACTGTCTTCCTCTACATTGTGGCACTGTGCAACTG
ACATAGACGACTAGTAGTAACACTGTAATAGATAGAGTAGGAAACCCAAAGCCAAAGGGGATGGATCTAACACAGCAAAGAAAACAT
GGATGTCATGCCATAACAATAATATCAATTATACCATTTGGATGGGACAAAGAAAAAAACTCTGGCAGACTTTTTGTTTTAATATTTTC
CATATTGCTGAAGCCCTAACTATAAGTCCTGAAGCACTTGTACTCAACTTTGTTTCTCTCCTCCTGGTCAG (SEQ ID NO. 1)
```

TILAPIA (*OREOCHROMIS NILOTICUS*) MYOSIN LIGHT CHAIN 3 PROMOTER

RELATED APPLICATIONS

This application claims the benefit of U.S. provisional application No. 62/067,298, filed Oct. 22, 2014 under 35 U.S.C. §119, the entire content of which is incorporated herein by reference.

FIELD OF THE INVENTION

The present invention relates to a new promoter to enhance target gene expression in specific tissues or a biomarker. In particular, the present invention relates to a tilapia (*Oreochromis niloticus*) myosin light chain 3 promoter in skeletal muscle of fish.

BACKGROUND OF THE INVENTION

Recombinant DNA technology has recently become a powerful technology for manipulating foreign genes in transgenic fish, and enables functional analysis of gene expression in specific organs, tissues, and cells. Moreover, control of target gene (transgene) expression is required to establish transgenic fish for used in molecular and immune-related studies, or to generate transgenic fluorescent ornamental fish (Hsieh, J C et al., Tilapia hepcidin (TH)2-3 as a transgene in transgenic fish enhances resistance to *Vibrio vulnificus* infection and causes variations in immune-related genes after infection by different bacterial species. Fish Shellfish Immunol 29:430-439, 2010). The choice of promoter is an important consideration for control of transgene expression.

Myosin is a complex multimeric protein that plays important roles in contractile processes in eukaryotes. Myosin comprises myosin heavy and light chains, which have multiple isoforms with different spatiotemporal expression patterns (Parker et al., Characterization of the myosin light-chain-2 gene of *Drosophila melanogaster*. Mol Cell Biol 5:3058-3068, 1985). Some well-studied promoters are reported, including myosin light chain (Mlc2; phosphorylatable) gene family. In mice, the Mlc2 family includes three genes, expressed in fast skeletal muscle, cardiac and slow skeletal muscle, and smooth muscle and non-muscle cells, respectively (Shani, M, Tissue-specific expression of rat myosin light-chain 2 gene in transgenic mice. Nature 314:283-286, 1985; Lee, K J et al., Myosin light chain-2 luciferase transgenic mice reveal distinct regulatory programs for cardiac and skeletal muscle-specific expression of a single contractile protein gene. J Biol Chem 267:15875-15885, 1992). These Mlc2 isoforms may be a suitable model for investigating muscle-specific gene expression during different developmental stages. The zebrafish Mylz2 promoter has traditionally been used to ensure the integrity and expression of foreign genes in transgenic fish (Pan, C Y et al., Transgenic expression of tilapia hepcidin 1-5 and shrimp chelonianin in zebrafish and their resistance to bacterial pathogens. Fish Shellfish Immunol 31:275-285, 2011); it has been used to drive expression of fluorescent proteins in the muscle tissue of zebrafish (Ju, B et al., Recapitulation of fast skeletal muscle development in zebrafish by transgenic expression of GFP under the mylz2 promoter. Dev Dyn 227:14-26, 2003; Zeng, Z et al., Faithful expression of living color reporter genes in transgenic medaka under two tissue-specific zebrafish promoters. Dev Dyn 234:387-392, 2005). However, the zebrafish Mylz2 promoter is not suitable for driving expression of transgenic fluorescent protein in other fish species, including the convict cichlid (*Archocentrus nigrofasciatus*), as it results in only weak fluorescence in muscle, and the promoter is weaker than promoters of bream species. One way to resolve these problems would be to use skeletal muscle myosin isoforms from a different fish species; certain isoforms have been isolated and characterized, and are available (Rowlerson, A et al., Comparative study of myosins present in the lateral muscle of some fish: species variations in myosin isoforms and their distribution in red, pink and white muscle. J Muscle Res Cell Motil 6:601-640, 1985). It is desired to develop or construct a new promoter for driving expression of transgenic fluorescent fishes.

SUMMARY OF THE INVENTION

Accordingly, the present invention provides a new promoter to target a fluorescent protein to the muscles of fish, such as *A. nigrofasciatus*, for ornamental purposes, which is a Mlc3 (myosin, light polypeptide 3, skeletal muscle) promoter.

The Mlc3 promoter has the nucleotides of tilapia (*Oreochromis niloticus*) myosin light chain 3 (Mlc3) promoter region with a size of about 4.3 kb, which has the nucleotide sequence of SEQ ID No. 1, and is potential to be a tilapia Mlc3 promoter to enhance protein expression in muscle of fish, particularly for the generation of ornamental fish.

In one aspect, the present invention provides a nucleic acid molecule, comprising the nucleotide sequence of SEQ ID No. 1, having a promoter activity in expression of a target protein in muscle.

In one example of the invention, the nucleic acid molecule is a Mlc3 (myosin, light polypeptide 3, skeletal muscle) promoter.

In another aspect, the invention provides a construct comprising the Mlc3 promoter fused to a nucleotide sequence coding for a target protein.

In one embodiment of the invention, the target protein is a luciferase protein. One example of the invention is a construct containing the Mlc3 promoter fused to a luciferase reporter gene.

In a further aspect, the invention provides a method for generating a transgenic fish, comprising the steps of:
(i) constructing the Mlc3 promoter of the invention ligated to a vector;
(ii) delivering the construct obtained in step (i) into embryos;
(iii) identifying the transgenic fish.

In a yet aspect, the invention provides a transgenic fish comprising a construct of the Mlc3 promoter fused to a nucleotide sequence coding for a target protein.

In one embodiment of the invention, the target protein is a fluorescent protein. One example of the invention is a luciferase reporter gene.

In one embodiment of the invention, the fish is *Archocentrus* sp., such as *A. nigrofasciatus*.

One example illustrating the transgenic fish according to the invention is a transgenic germline carrying Taiwan coral red fluorescent protein (TcRFP) driven by the Mlc3 promoter, which was established in the ornamental fish species *A. nigrofasciatus* var. The F1 adult transgenic *A. nigrofasciatus* var. exhibited brilliant pink fluorescence in skeletal muscle that was observable under visible light, and thus may be suitable for ornamental exhibition.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

FIGS. 1a and 1b show the nucleotide sequence of SEQ ID NO. 1 and the structure of the Mlc3 promoter according to the invention.

FIG. 1a provides the nucleotide sequence of the Mlc3 promoter having the nucleotide sequence of SEQ ID NO. 1 according to the invention.

Figures 1, 1B, 2, 3:
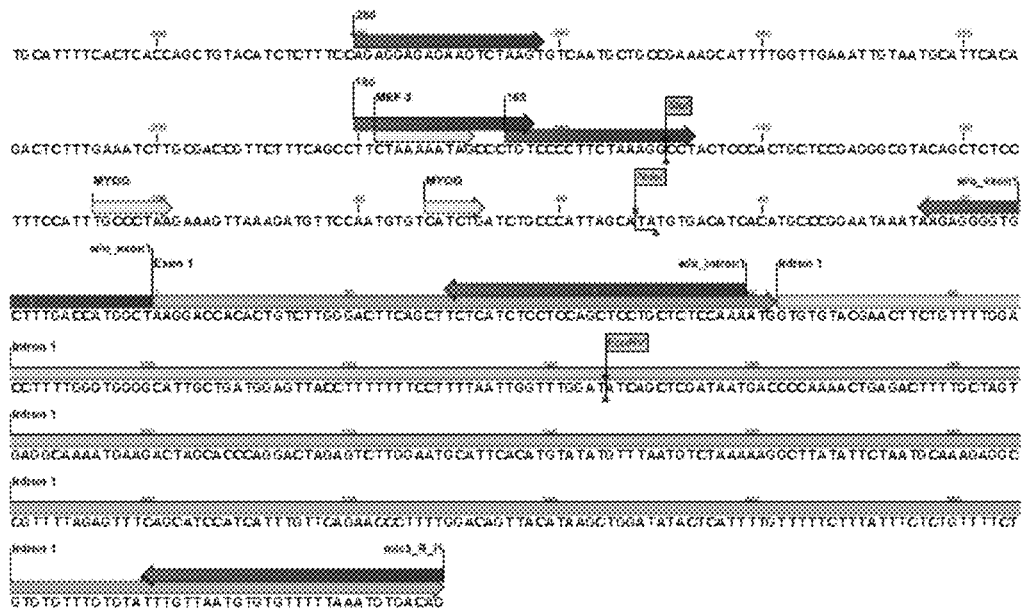

FIG. 1b provides a scheme showing the Mlc3 promoter according to the invention containing the 5' flanking region of the O. niloticus Mlc3 gene, wherein the first nucleotide of the transcription start is designated +1, the green arrow indicates exon 1; the turquoise arrow indicates intron 1; the red arrows indicate the locations of primer sequences; the yellow arrows indicate transcription factor-binding sequences; and the boxes indicate restriction enzyme sites.

Figure 2A:
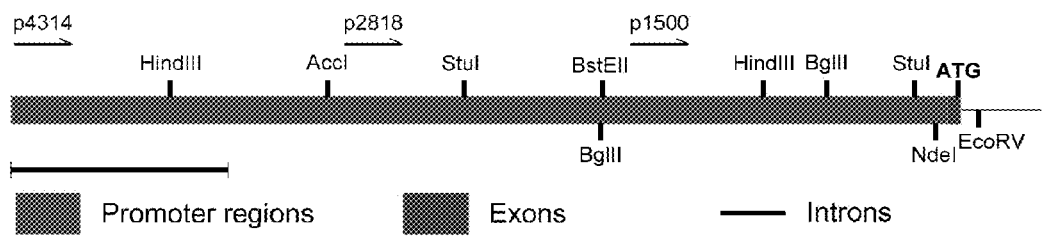
Figure 2B:
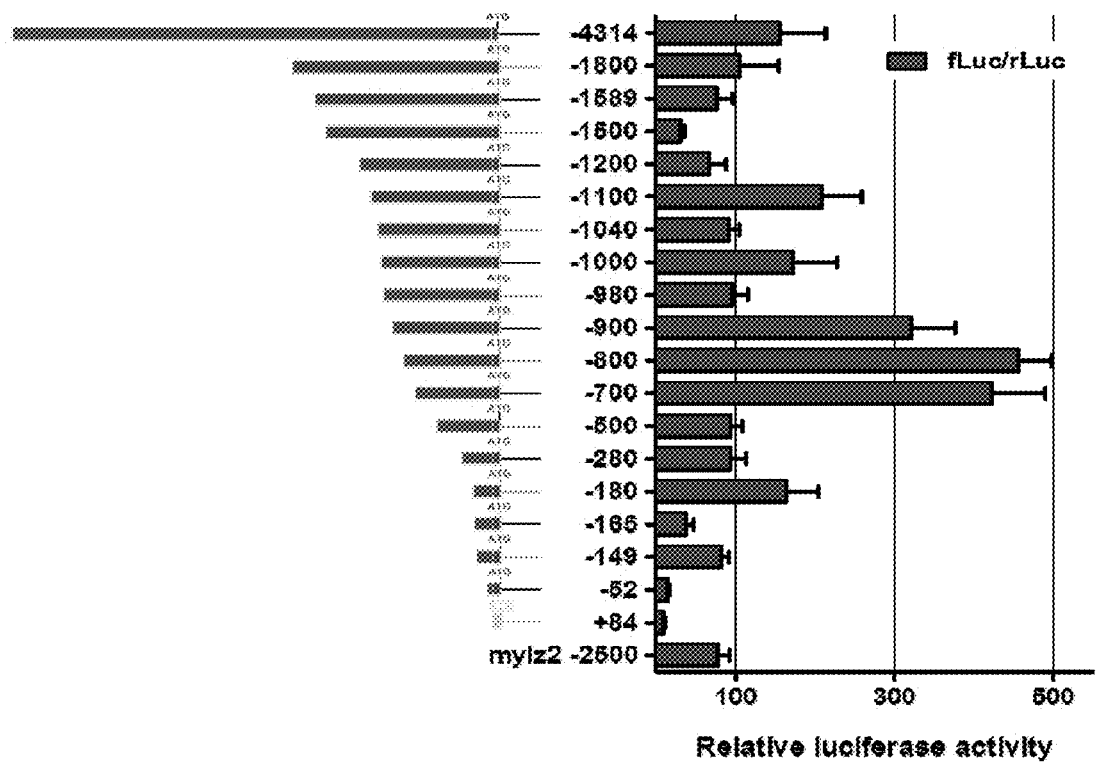
Figure 3:
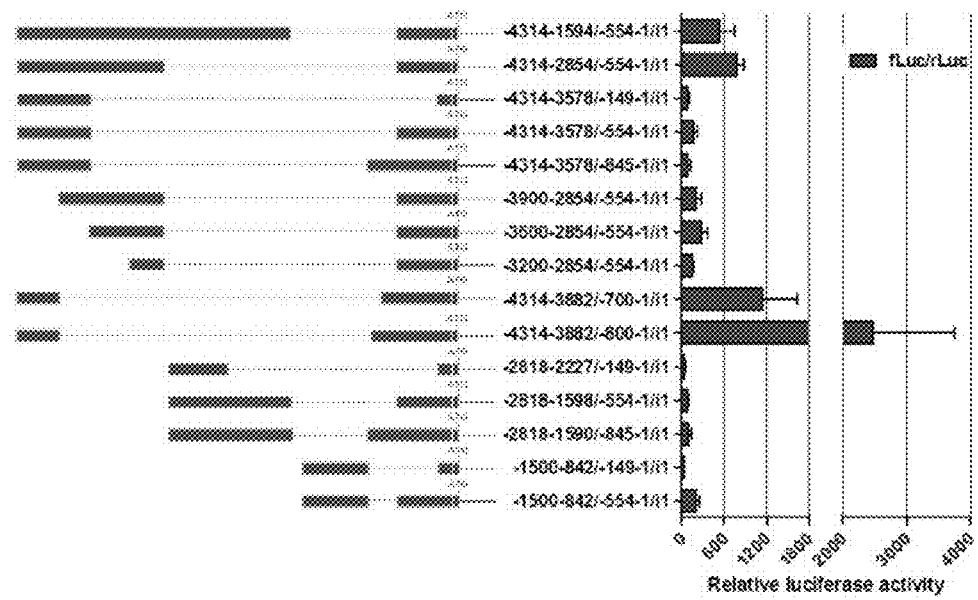

FIGS. 2a and 2b show the activity of the promoter regions of the tilapia myosin light chain 3 (Mlc3) gene.

FIG. 2a provides the restriction enzyme map of the Mlc3 promoter containing the promoter regions, exon 1 and intron 1.

FIG. 2b shows the activity of 19 different promoter regions of the tilapia myosin light chain 3 (Mlc3) gene; wherein the numbers next to each promoter construct indicate its most 5' position, relative to the transcription start site. The promoter fragments (shown in blue) were fused to the luciferase reporter gene, and the vectors were directly injected into Archocentrus nigrofasciatus muscle. Relative luciferase activity was measured 96 h later, and normalized for transfection efficiency against Renilla activity (fLuc/rLuc) to control for transfection efficiency. The Mylz2-2500 fragment was cloned from the zebrafish Mylz2 promoter (Peng, K C et al., Using an improved Tol2 transposon system to produce transgenic zebrafish with epinecidin-1 which enhanced resistance to bacterial infection. Fish Shellfish Immunol 28:905-917, 2010). All data represent the mean of at least 3 replicates.

FIG. 3 shows the activity of deletion constructs of the tilapia myosin light chain 3 (Mlc3) gene promoter. The different fragments of the 5'-flanking region containing regions from -4314 to -1954 and from -554 to -1 bp relative to the transcription start site (shown in blue) were fused to a luciferase reporter gene, and the various constructs were directly injected into Archocentrus nigrofasciatus muscle. Relative luciferase activity was measured 96 h later, and normalized for transfection efficiency against Renilla activity (fLuc/rLuc). All data represent the mean±SE of at least 3 experiments.

Figure 4:
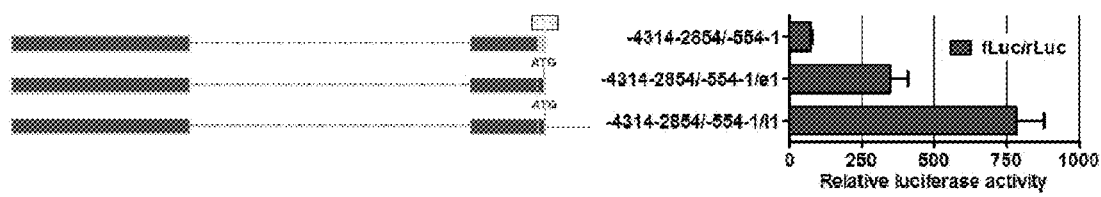

FIG. 4 shows the activity of tilapia myosin light chain 3 (Mlc3) gene promoters with or without exon and intron sequences. The different fragments of the 5'-flanking region from -4314 to -2854 and -554 to -1 bp relative to the transcription start site were fused to a luciferase reporter gene. The constructs contained intron 1 and exon 1 (-4314-2854/-554-1/i1), exon 1 alone (-4314-2854/-554-1/e1), or neither exon 1 nor intron 1 (-4314-2854/-554-1). The vectors were directly injected into Archocentrus nigrofasciatus muscle. Relative luciferase activity was measured 96 h later, and normalized for transfection efficiency against Renilla activity (fLuc/rLuc). All data represent the mean±SE of at least 3 experiments.

Figure 5:
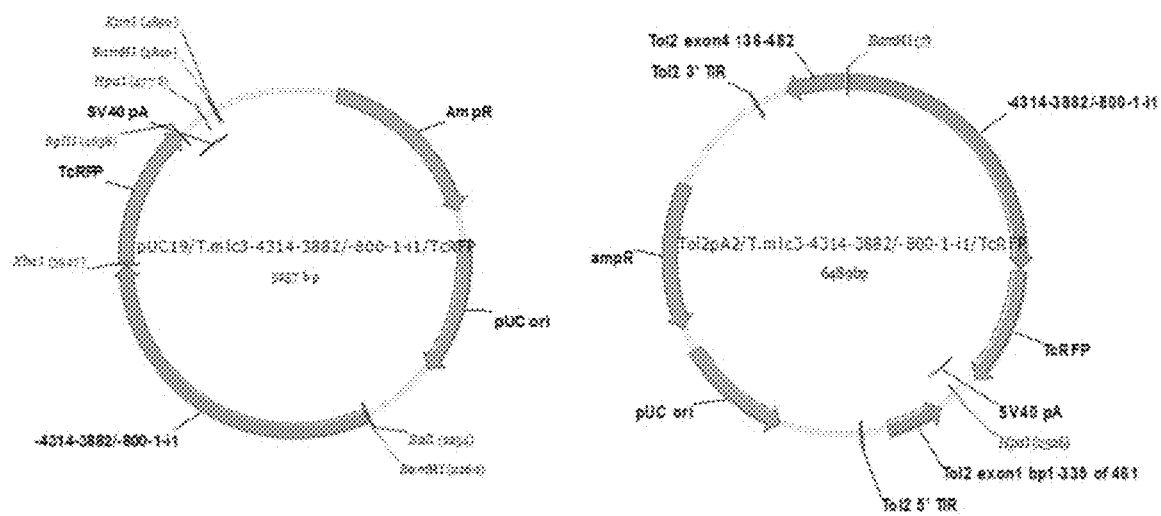

FIG. 5 provides one example of the ornamental expression of fluorescent protein in transgenic Archocentrus nigrofasciatus var, which provides the construction containing Taiwan coral red fluorescent protein (TcRFP) that was ligated to a tilapia myosin light chain 3 (Mlc3) promoter region (-4314-3882/-800-1/i1), and cloned into the pUC19 plasmid. This vector and the Tol 2 system plasmid were then cut with BamHI and HpaI restriction enzymes, and ligated to generate Tol2pA2/T.mlc3-4314-3882/-800-1-i1/TcRFP. This vector was used to produce transgenic fluorescent A. nigrofasciatus var.

DETAILED DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "promoter" refers to an untranslated DNA sequence upstream of a coding region that contains the binding site for an RNA polymerase and initiates transcription of the coding region. The promoter region may also include other elements that act as regulators of gene expression.

The present invention provides a new promoter to target a fluorescent protein to the muscles of fish, such as A. nigrofasciatus, for ornamental purposes, which is a Mlc3 (myosin, light polypeptide 3, skeletal muscle) promoter.

According to the present invention, the Mlc3 promoter is cloned and characterized. The Mlc3 promoter has the nucleotide sequence of SEQ ID NO. 1 as shown in FIG. 1a. The sequence of the Mlc3 promoter is similar to a tilapia gene, Mlc3, skeletal muscle isoform-like from Nile tilapia (O. niloticus), with high similarity at a 51 bp region at the 3' end of the tilapia Mlc3 flanking region, with the exception of exon 1 (see FIG. 1b). The Mlc3 promoter contains several putative transcription factor-binding sites in the promoter region, including binding sites for MYOG (Myogenin (myogenic factor 4)), MyoD, MEF-2, PKNOX1, and AREB6 (see FIG. 1b). It was unexpectedly found that the promoter activity was enhanced as determined by direct injection of a luciferase reporter construct into skeletal muscle of A. nigrofasciatus.

A construct or an expression cassette comprising the Mlc3 promoter can be generated recombinantly or synthetically for expression of a target protein, with a series of specified nucleic acid elements which permit transcription of a nucleotide sequence coding for a target protein in a host. The construct or expression cassette can be incorporated into a vector such as a plasmid, chromosome, mitochondrial DNA, plastid DNA, virus, or nucleic acid fragment.

As illustrated in the examples of the invention, stable transgenic germlines carrying Taiwan coral red fluorescent protein (TcRFP) driven by the Mlc3 promoter were established in the ornamental fish species A. nigrofasciatus var. The F1 adult transgenic A. nigrofasciatus var. exhibited brilliant pink fluorescence in skeletal muscle that was observable under visible light, and thus may be suitable for ornamental exhibition. Therefore, the present invention provides a good promoter to generate fluorescent ornamental fish of species such as Perciformes, by applying gene-transfer technology.

According to the present invention, the transgenic animal is preferably a fish, more preferably Perciformes, such as *Archocentrus* sp., most preferably *A. nigrofasciatus*.

Generation of transgenic animals of the present invention is carried out conventionally by techniques well known in the art. There are a number of techniques that permit the introduction of genetic material (such as a transgene) into animals to be transformed, including the viral infection technique; the sperm mediated gene transfer (SMGT) technique; the embryonic stem cell technique; the nuclear transfer technique; and the pronuclear microinjection technique. Among them, the most commonly used technique is the pronuclear microinjection technique. According to a preferred embodiment of the present invention, the nucleotide sequence coding for a target gene is introduced into the embryo by microinjection.

The present invention is further illustrated by the following examples, which are provided for the purpose of demonstration rather than limitation.

EXAMPLES

Materials and Methods

Polymerase Chain Reaction (PCR) Cloning and Sequence Analyses

The sequence of the myosin, light chain 3, skeletal muscle (Mlc3) promoter region was determined by PCR, using tilapia genomic DNA as template. Genomic DNA was extracted from muscle of tilapia, and genomic DNA cloning of the tilapia Mlc3 promoter region was performed as described previously (Peng et al. 2010). In brief, Mlc3 DNA sequences from different cichlid species were obtained from the NCBI database (http://www.ncbi.nlm.nih.gov/), and used as probes to screen the Cichlid Genome Resources database (http://cichlid.umd.edu/blast/blast.html/) with BLASTN algorithms. The retrieved scaffold sequence was used to design the following primer pair:

```
                                            (SEQ ID NO. 2)
5'-ttctcttttcttcctctgtgggaccat-3' (forward)
and (SEQ ID NO. 3)
5'-ctgtcacatttaaaaacacacattaacaaa-3' (reverse).
```

The PCR product was cloned using a CloneJET PCR cloning kit (Fermentas, www.fermentas.com) and the clone was sequenced.

Gene Constructs

For functional assays, PCR-amplified 5'-promoter regions of the tilapia gene were cloned using a CloneJET PCR cloning kit (Fermentas) and subcloned using a Tol2 kit by BP reaction (a multisite gateway-based construction kit for Tol2 transposon transgenic constructs). The primers mlc3_p4314 (5'-ggggacaactttgtatagaaaagttggctagct-tctcttttcttcctctgtgggaccat-3' (SEQ ID NO. 4)), mlc3p2818 (5'-ggggacaactttgtatagaaaagttggctagctactgacaataccaggccct gaagcaga-3' (SEQ ID NO. 5)), mlc3_p1500 (5'-gggga-caactttgtatagaaaagttggctagcgcgactgtc agacaaataaccacaacaa-3' (SEQ ID NO. 6)) and mlc3_R_i1 (5'-ggggactgctttttgta-caaacttgctg tcacatttaaaaacacacattaacaaa-3' (SEQ ID NO. 7)), wherein all forward primers contained one NheI site, were used.

These promoter entry clones were used to construct reporter plasmids containing pME-Luc (firefly *Photinus pyralis* luciferase) and p3E-polyA by an LR reaction, and the resulting plasmids were named as follows:
pDestTol2pA2/T.mlc3-p-4314-i1/Luc,
pDestTol2pA2/T.mlc3-p-2818-i1/Luc, and
pDestTol2pA2/T.mlc3-p-1500-i1/Luc.

The pDestTol2pA2/TK/Rluc (containing pRL *Renilla* luciferase) reporter plasmid was constructed by an LR reaction, using p5E-TK, pME-RLuc, and p3E-polyA. The pDestTol2pA2/T.mlc3-p-4314-i1/Luc plasmid was digested with NheI and one of the following restriction endonucleases: BstEII (-1589), StuI (-149), NdeI (-52), or EcoRV (+84). These fragments were treated with a DNA blunting enzyme from the CloneJET PCR cloning kit (Fermentas), and self-ligated using T4 DNA ligase (Fermentas). pDestTol2pA2/T.mlc3-p-4314-i1/Luc was amplified using Phusion® High-Fidelity DNA polymerase (Finnzymes), and self-ligated with T4 DNA ligase (Fermentas).

The backbone primer attR4_shared (5'-CAACTTTTC-TATACAAAGTTGATAGCT TGG (SEQ ID NO. 8), 5' phosphorylation), and other primers shown in Table 1 were used. Deletion fragments generated using a single cutting site used their original promoter entry clones as templates, and were self-ligated with T4 DNA ligase (Fermentas) after digestion with the restriction enzymes indicated in parentheses, as follows:
pDestTol2pA2/T.mlc3-p-4314-1594/-554-1-i1/Luc (BglII),
pDestTol2pA2/T.mlc3-p-4314-35781-845-1-i1/Luc (HindIII),
pDestTol2pA2/T.mlc3-p-2818-2227/-149-1-i1/Luc (StuI), and
pDestTol2pA2/T.mlc3-p-2818-15981-554-1-i1/Luc (BglII).

The ends of deletion fragments generated using double restriction endonuclease (RE) cutting sites were blunted after being digested, and then selfligated; and are named as follows:
pDestTol2pA2/T.mlc3-p-4314-2854/-554-1-i1/Luc (AccI, BglII),
pDestTol2pA2/T.mlc3-p-4314-35781-149-1-i1/Luc (HindIII, StuI),
pDestTol2pA2/T.mlc3-p-4314-35781-554-1-i1/Luc (HindIII, BglII),
pDestTol2pA2/T.mlc3-p-2818-15901-845-1-i1/Luc (BstEII, HindIII),
pDestTol2pA2/T.mlc3-p-1500-8421-149-1-i1/Luc (HindIII, StuI), and
pDestTol2pA2/T.mlc3-p-1500-8421-554-1-i1/Luc (HindIII, BglII).

The plasmids containing exon 1, intron 1, or an initiation site downstream of the first DNA sequence were generated. These plasmids as generated were named as follows: -4314-2854/-554-1 (initiation site downstream of the first DNA sequence), -4314-2854/-554-1/e1 (containing the exon 1 region), and -4314-2854/-554-1/i1 (containing the intron 1 region).

The pDestTol2pA2/T.mlc3-p-4314-28541-554-1-i1/Luc was used as the template plasmid, and Luc-phosph (5'-CAAGTTTGTACAAAAAAGCAGGCTTAGCCA (SEQ ID NO. 9), 5' phosphorylation) was used as a backbone primer. PCR was performed as described previously (Peng et al., 2010). The primers used for the promoter activity assay are shown in Table 1 and FIG. 1b, and were synthesized by Quality Systems (Taipei, Taiwan).

TABLE 1

Sequence of Primers used in the present invention

| Primer | SEQUENCE | SEQ ID NO. |
|---|---|---|
| mlc3_p4314 | GGGGACAACTTTGTATAGAAAAGTTGGCTAGCTTCTCTTTTTCTTC CTCTGTGGGACCAT | SEQ ID NO. 4 |
| mlc3_p2818 | GGGGACAACTTTGTATAGAAAAGTTGGCTAGCTACTGACAATACAG GCCCTGAAGCAGA | SEQ ID NO. 5 |
| mlc3_p1500 | GGGGACAACTTTGTATAGAAAAGTTGGCTAGCGCGACTGTCAGACA AATAACCACAACAA | SEQ ID NO. 6 |
| mlc3_R_i1 | GGGGACTGCTTTTTTGTACAAACTTGCTGTCACATTTAAAAACACA CATTAACAAA | SEQ ID NO. 7 |
| mylz2_p2504 | GGGGACAACTTTGTATAGAAAAGTTGATGCTGTGAAGTATTCTCTA | SEQ ID NO. 10 |
| mylz2_R | GGGGACTGCTTTTTTGTACAAACTTGGTAGTGTCCTGTACTTGAGG | SEQ ID NO. 11 |
| 3900 | CGGTCGACAGGCAGCCTAGCAGCACTA | SEQ ID NO. 12 |
| 3600 | CGGTCGACAGTTTGTACAATTCTGTCAA | SEQ ID NO. 13 |
| 3200 | CGGTCGACTAGCTGGTATTTATACAT | SEQ ID NO. 14 |
| 1800 | CGGTCGACAATTCGAACCAAGAGTCTAA | SEQ ID NO. 15 |
| 1200 | CGGTCGACTTCTTATAAACCACGGAGA | SEQ ID NO. 16 |
| 1100 | GTTGGGTAATAATTGTATATGA | SEQ ID NO. 17 |
| 1040 | CGGTCGACTTGTTGCTTTTGAAATTGTG | SEQ ID NO. 18 |
| 1000 | AAATAACTTGAAAAATAAAACT | SEQ ID NO. 19 |
| 980 | CGGTCGACCTGCACTTGGAGAATCAGAG | SEQ ID NO. 20 |
| 900 | AAATTAAGTTTGTTACATCA | SEQ ID NO. 21 |
| 800 | CCATGGAGAGCTCTGCTGA | SEQ ID NO. 22 |
| 700 | CGGTCGACTTATGTAAGTTTAACTTT | SEQ ID NO. 23 |
| 500 | CGGTCGACGCCGCTCAGTGTCAATGCT | SEQ ID NO. 24 |
| 280 | CGGTCGACAGAGGAGAGAAGTCTAAGT | SEQ ID NO. 25 |
| 180 | CGGTCGACTTCTAAAAATAGCCCTGT | SEQ ID NO. 26 |
| 165 | CGGTCGACTGTCCCCTTCTAAAGGCCT | SEQ ID NO. 27 |
| attR4_shared | CAACTTTTCTATACAAAGTTGATAGCTTGG (5' phosphorylation) | SEQ ID NO. 28 |
| 3900R | TAGTGCTGCTAGGCTGCCTAACTTGT (5' phosphorylation) | SEQ ID NO. 28 |
| Luc-phosph | CAAGTTTGTACAAAAAAGCAGGCTTAGCCA (5' phosphorylation) | SEQ ID NO. 29 |
| w/o_exon1 | AGCCATGGTCAAAGCACCCCTCTT | SEQ ID NO. 29 |
| w/o_intron1 | TTTGGAGAGCAGGAGCTGGAGGAG | SEQ ID NO. 30 |
| F_Tmlc3-p-4314_SalI_BamHI | AGGCGTCGACGGATCCTTCTCTTTTTCTTCCTCTGT | SEQ ID NO. 31 |
| R_Tmlc3-i1_XbaI | CATCTAGACTGTCACATTTAAAAACACA | SEQ ID NO. 32 |
| F_11-2FP_XbaI | GGTCTAGAATGGCTCTGTCAAAGCACGGT | SEQ ID NO. 33 |
| R_11-2FP_BglII | GTAGATCTTTATCCGGGCAATGCGGAT | SEQ ID NO. 34 |

To generate transgenic fluorescent fish, the tilapia Mlc3 promoter region were ligated to the TcRFP fluorescent protein gene (wherein the plasmid was acquired from Dr. Ming-Chyuan Chen, at Department of Marine Biotechnology, National Kaohsiung Marine University, Kaohsiung 811, Taiwan (unpublished results). The tilapia Mlc3 promoter region (-4314-3882/-800-1-i1) was ligated to TcRFP in the pUC19 plasmid, to generate pUC19/T.mlc3-4314-3882/-800-141/TcRFP (FIG. 5a, left). This plasmid was then cut with BamHI and HpaI, and the TcRFP construct sub-cloned into the Tol2 vector to generate Tol2pA2/T.mlc2-4314-38821-800-1-i1/TcRFP (FIG. 5a, right).

Injection of Tilapia Myosin, Light Chain 3, Skeletal Muscle (Mlc3) Promoter Region into *A. nigrofasciatus* Muscle and Promoter Assay Deletion fragments containing various lengths of the tilapia Mlc3 promoter region ligated to luciferase were constructed. Plasmids with various lengths of the Mlc3 promoter region were as follows: -4314, -1800, -1589, -1500, -1200, -1100, -1040, -1000, -980, -900, -800, -700, -500, -280, -180, -165, -149, -52, and +84 (see FIG. 1b, and FIG. 2b). The initiation site was defined as +1. Mylz2-2500 indicates the zebrafish Mylz2 2.5-kb-long promoter region from our previous study (Peng et al., 2010). Deletion fragments between the intermediate zone of the Mlc3 promoter region were as follows: -4314-1594/-554-1/i1, -4314-2854/-554-1/i1, -4314-3578/-149-1/i1, -4314-3578/-554-1/i1, -4314-3578/-845-1/i1, -3900-2854/-554-1/i1, -3600-2854/-554-1/i1, -3200-2854/-554-1/i1, -4314-3882/-700-1/i1, -4314-3882/-800-1/i1, -2818-2227/-149-1/i1, -2818-1598/-554-1/i1, -2818-1590/-845-1/i1, -1500-842/-149-1/i1, -1500-842/-554-1/i1, -4314-2854/-554-1, -4314-2854/-554-1/e1, and -4314-2854/-554-1/i1 (see FIGS. 1b, 3, 4).

These numbers can be compared to the sequence information in Figure to identify the region. For example, -4314-2854 indicates a fragment between -4314 and -2854 bp. The designation "i1" indicates that the plasmid includes the intron 1 region. The designation "e1" indicates that the plasmid includes the exon 1 region. The fragment -4314-2854/-554-1 does not contain exon 1 or intron 1. Each *A. nigrofasciatus* embryo was injected with 2.61×10-6 μmole of a reporter plasmid (FIGS. 2, 3, 4) and the pDestTol2pA2/TK/Rluc vector (each fish was injected with 4 μg). The latter was used as an internal control, and contained the *Renilla* Luciferase Control Reporter mixture. After injection, fish were maintained in water for 96 h and then subjected to the luciferase assay. Fish used had body lengths of 5 cm. The head and internal organs of each fish were removed, and an equal weight of passive lysis buffer was added to the muscle (for example, 1 ml of buffer was added to 1 g of fish weight). The mixtures were homogenized, and each fragment was placed in a tube; the sample was mechanically disrupted with passive lysis buffer (Promega, Madison, Wis., USA) on ice. This was centrifuged at 13,000 rpm for 10 min, and 2 μl of the resulting supernatant was mixed with 50 μl of luciferase assay reagent II (Promega); emission was then measured with a Fluoroskan Ascent FL luminometer (Thermo Labsystems, Ramsey, Minn., USA). Promoter analysis values are presented as the mean±SEM.

Microinjection and Development of Transgenic Pink Fluoresence *A. nigrofasciatus* Var The Mlc3/TcRFP plasmid (pUC19/T.mlc3-4314-3882/-800-141/TcRFP) (FIG. 5a, left panel) was constructed by amplifying the Mlc3 promoter by PCR as described above, and ligating it into the Tol2pA2 vector via BamHI and HpaI RE sites (FIG. 5a, right panel). Plasmid DNA of Mlc3/TcRFP (Tol2pA2/T.mlc3-4314-3882/-800-141/TcRFP; see FIG. 5) was injected into the one-cell stage of ~200 *A. nigrofasciatus* var. eggs with transposase mRNA; after injection, the eggs were placed in a 28° C. incubator. The whole body of *A. nigrofasciatus* var. was examined by fluorescence microscopy using an FITC filter (IX71; Olympus, Tokyo, Japan) every 120 min. Fish were cultured in water at a temperature of 26~29° C. The pH value ranged from 6.6~7.8. The photoperiod was fixed at 12-h light/12-h dark. Prior to 30 days post-fertilization (dpf), embryos were fed on brine shrimp, while 3~16-week-old fish were fed ayu feed (Fry Early, Uni-president Group, Taiwan), and adult fish were fed Tetra Bits (Tetra, Germany).

Results

Tilapia Mlc3

Using a primer (p4314) and exon 2 (Table 1), we cloned a 5' Mlc3 promoter region including exon 1 and partial intron 1 sequences (see FIGS. 1a and 1b). BLASTN analysis revealed that the sequence was Mlc3, skeletal muscle isoform-like from Nile tilapia (*O. niloticus*) (GenBank XM_003453183.1 and AERX01030583.1). Approximately 51 bp at the 3' end of tilapia Mlc3 flanking region was identical to the published sequence, with the exception of exon 1 (FIG. 1b).

A search of the TRANSFAC (http://www.gene-regulation.com/pub/databases.html) database revealed many putative transcription factor-binding sites in the promoter region, including binding sites for MYOG (Myogenin (myogenic factor 4)), MyoD, MEF-2 (myocyte-specific enhancer factor), PKNOX1, and AREB6 (FIG. 1b).

Tilapia Mlc3 Gene Promoter Activity

To determine which regions of the tilapia Mlc3 5' end confer promoter activity, we constructed sequential 5' deletions of the putative promoter region, either with or without the transcription start site ligated to the luciferase coding sequence (FIG. 2b).

Plasmids containing the various constructs were injected into *A. nigrofasciatus* muscle, and relative luciferase activity was measured 96 h later. Minimal luciferase activity was observed with promoter regions +84, -52, -165, -1500, and -1200 (positions are relative to the transcription start site), while it was much higher with the -900, -800, and -700 fragments (FIG. 2b). We next asked whether deletions in the promoter intermediate zone had any effects on luciferase activity through deletion of myogenic- or myocyte-related transcription factor-binding sequences. The -4314-3882/-800-1/i1 construct exhibited a significant increase (150-fold) in luciferase activity as compared to that of the -1500-842/-149-1/i1 construct fragment (FIG. 3).

The -4314-3882/-800-1/i1 construct contains one MYOG and two MEF-2 binding sequences between -4314 and -3882 bp, and two MYOG and three MEF-2 binding sequences between -149 and -1 bp. These results suggest that the region between -700 and -800 bp may contain strong positive regulatory elements, and the region between -3882 and -800 bp may contain negative regulatory elements. To establish whether the region containing intron 1 or exon 1 enhances promoter activity, we constructed three different constructs containing (i) intron 1; (ii) exon 1 alone; or (iii) neither intron 1 nor exon 1. Luciferase reporter activity was driven by the same promoter fragment for each construct (FIG. 4). A 2.1~-5.9-fold increase in luciferase activity was observed for the -4314-2854/-554-1/i1 (intron 1) construct as compared to the -4314-2854/-554-1 (no exon and intron) or -4314-2854/-554-1/e1 (exon 1 only) constructs (FIG. 4), indicating that partial intron 1 and exon 1 sequences enhance promoter activity.

Intense Pink Fluorescence in Live Transgenic *A. nigrofasciatus* Var.

We proceeded to examine the possibility of using the -4314-3882/-800-1-i1 promoter construct to generate transgenic ornamental fish. The -4314-3882/-800-1-i1 construct was ligated to the TcRFP reporter in the Tol2 plasmid (FIG. 5), and the plasmid was delivered into one-cell embryos by microinjection. We initially obtained eleven transgenic *A. nigrofasciatus* var. nine of which survived. The survivors (F0) were mated with wild-type (WT) *A. nigrofasciatus* var. to establish transgenic lines (F1 strain). Only one transgenic F0 parent (9 dpf) transmitted strong fluorescence to its offspring. In the F1 generation (60 dpf), the pink fluorescence was bright and readily observed under normal daylight.

It is illustrated in the examples that the Nile tilapia (*O. niloticus*) gene can be expressed with high levels in skeletal muscle, in order to create fluorescent ornamental fish or to enhance protein expression in muscle. In the present invention, the myosin, light chain 3, skeletal muscle (Mlc3) promoter region was cloned, because in contrast to many other musclerelated promoters, the structure is simple with a short sequence. The Mlc3 promoter is capable of driving high expression of transgenes. Previously, the zebrafish Mylz2 promoter was used to drive GFP expression in *A. nigrofasciatus, Gymnocorymbus ternetzi*, medaka, and zebrafish (Zeng et al. 2005; Pan et al. 2008; Hsieh et al. 2010; Peng et al. 2010), and muscle-specific expression patterns were detected in the species tested. However, when we used the zebrafish Mylz2 promoter to drive TcRFP expression by a single microinjection into *A. nigrofasciatus* fertilized eggs, we observed weak fluorescence in the F0 generation. In addition, a previous publication reported that zebrafish Mylz2 promoter-driven expression of RFP in *G. ternetzi* body muscles was patchy (Pan et al. 2008). Although stable fluorescent transgenic *Oryzias dancena* lines in which RFP is driven by the *O. dancena* myosin light chain 2 promoter have been generated previously (Cho Y S et al., Characterization of stable fluorescent transgenic marine medaka (*Oryzias dancena*) lines carrying red fluorescent protein gene driven by myosin light chain 2 promoter. Transgenic Res (PMID:23188170), 2012), this promoter has not been used to produce fluorescent protein in other fish species. Hence, there is still a need to identify stronger muscle-specific, cross-species promoters for use in transgenic fish development.

In the present invention, we isolated and characterized the tilapia Mlc3 gene (62 bp), including 4.3 kb of its promoter region (FIG. 1b). Inspection of this promoter region revealed binding sequences for MYOG, MEF-2, MyoD, PKNOX1 and AREB6, among other transcription factors. The binding sequences of PKNOX1 and AREB6 are not, however, found in the zebrafish MLC2f (myosin light chain 2) gene (Xu Y et al., Fast skeletal muscle-specific expression of a zebrafish myosin light chain 2 gene and characterization of its promoter by direct injection into skeletal muscle. DNA Cell Biol 18:85-95, 1999). The zebrafish MLC2f gene is expressed in embryos and adult fish, and is specifically expressed in fast skeletal muscles (Xu et al. 1999). Comparison of the 1.4-kb upstream region of zebrafish or *Sparus aurata* MLC2 with that of tilapia Mlc3 revealed that, in addition to consensus sequences such as the MEF-2 binding site, MyoD binding sites also existed in these promoter regions (Xu et al. 1999; Funkenstein et al., Characterization and functional analysis of the 5' flanking region of myosin light chain-2 gene expressed in white muscle of the gilthead sea bream (*Sparus aurata*). Comp Biochem Physiol Part D Genomics Proteomics 2:187-199, 2007). Binding of the MEF-2 transcription factor plays an important role in activating many cardiac and skeletal muscle-specific promoters/enhancers, and also acts as a key regulator in cardiac and skeletal muscle lineages (Gossett et al., A new myocyte-specific enhancer-binding factor that recognizes a conserved element associated with multiple muscle-specific genes. Mol Cell Biol 9:5022-5033, 1989; Cserjesi, P and Olson, E N, Myogenin induces the myocyte-specific enhancer binding factor MEF-2 independently of other muscle-specific gene products. Mol Cell Biol 11:4854-4862, 1991). Another report suggested that MEF-2 is a regulator of myogenic bHLH genes (Edmondson D G et al., Analysis of the myogenin promoter reveals an indirect pathway for positive autoregulation mediated by the muscle-specific enhancer factor MEF-2. Mol Cell Biol 12:3665-3677, 1992). The tilapia Mlc3 promoter contains two putative MEF-2 binding sequences between -4314 and -3882 bp, and two putative MEF-2 binding sequences between -800 and -1 bp. These MEF-2-binding sequences may be required to enhance activation, according to our in vivo promoter analysis. The MEF-2 and bHLH transcription factors can co-activate many skeletal muscle-specific genes, and are involved in myogenesis (Arnold, H H and Winter, B, Muscle differentiation: more complexity to the network of myogenic regulators. Curr Opin Genet Dev 8:539-544, 1998; Black, B L and Olson, E N, Transcriptional control of muscle development by myocyte enhancer factor-2 (MEF2) proteins. Annu Rev Cell Dev Biol 14:167-196, 1998). In addition, MyoD and MEF-2 bound to DNA in vivo are efficient muscle-specific promoters (Fickett, J W, Coordinate positioning of MEF2 and myogenin binding sites. Gene 172:GC19-32, 1996). As a region within 79 bp of the proximal promoter region and 3 kb of the promoter region of the zebrafish MLC2f gene was found to be sufficient for high levels of expression in muscle cells, it was previously suggested that no other enhancers exist within the 3-kb promoter (Xu et al. 1999). However, the presence of enhancers outside of this 3-kb region cannot be ruled out, as we identified regulatory sequences outside of the tilapia Mlc3 promoter.

In the present invention, we injected DNA (promoter fragments) into *A. nigrofasciatus* muscle, and found that tilapia Mlc3 is a muscle-specific promoter. These results indicate that, despite the low DNA sequence similarity of proximal promoter sequences between the tilapia Mlc3 and zebrafish Mylz2, they both result in muscle-specific expression. It is suggested that transient promoter activity analysis is an effective and reliable system to study muscle-specific promoter activity (Tan, J H, and Chan, W K, Efficient gene transfer into zebrafish skeletal muscle by intramuscular injection of plasmid DNA. Mol Mar Biol Biotechnol 6:98-10, 1997; Funkenstein et al. 2007). This experimental method was pioneered using DNA directly injected into skeletal muscle of mice (Wolff, J A et al., Direct gene transfer into mouse muscle in vivo. Science 247:1465-1468, 1990). This technique was used to *A. nigrofasciatus*. Spatial and temporal patterns of TcRFP expression during larval and adult development were similar for all live transgenic *A. nigrofasciatus* var. of the F1 generation. The signal became stronger throughout development, and in the adult, the intense pink fluorescence was found in the whole body, with the exception of the eyes, head/jaw, and fins. Overall TcRFP expression patterns in live transgenic *A. nigrofasciatus* var. were consistent with zebrafish Mylz2 promoter-driven GFP expression patterns in *A. nigrofasciatus* (F3 generation) (Hsieh et al. 2010) and expression patterns of other Mlc2 promoter-driven fluorescent proteins in different transgenic fish strains, including: zebrafish Mylz2 promoter-driven RFP in *Gymnocorymbus ternetzi* (patchy expression in body muscles) (Pan et al. 2008); zebrafish Mylz2 promoter-driven RFP in zebrafish (expression in whole-body muscle) (Peng et al. 2010); *O. dancena* Mylc2f promoter-driven RFP in *O. dancena* (expression in body muscle) (Cho et al. 2012); and medaka Mylz2 promoter-driven GFP in transient transgenic zebrafish embryos (expression in skeletal muscle) (Zeng et al. 2005). The intensity of the fluorescence in *A. nigrofasciatus* var. was comparable to that of other transgenic fish with different muscle-specific promoters, and exhibited patchy expression due to mosaicism in transgenic founders, resulting from an uneven distribution of injected DNA (Westerfield, M et al., Specific activation of mammalian Hox promoters in mosaic transgenic zebrafish. Genes Dev 6:591-598, 1992; Udvadia, A J and Linney, E, Windows into development: historic, current, and future perspectives on transgenic zebrafish. Dev Biol 256:1-17, 2003). It is illustrated that stable transgenic germlines of *A. nigrofasciatus* var. carrying a tilapia Mlc3 promoter-driven TcRFP transgene was generated. We also applied a functional promoter assay originally developed for muscle tissues to whole fish, thus providing information on tissue-specific patterns of gene regulation.

Furthermore, it is also deduced that the region between -4314 and -3882 and between -1 and -800 bp may contain positive regulatory elements by comparing luciferase activities; sequence analysis revealed that these regions contain MEF-2 and MYOG binding sites, which could enhance activity.

It was concluded in the present invention that the tilapia Mlc3 promoter may play an important role in muscle development. Furthermore, fluorescent transgenic *A. nigrofasciatus* var. has great potential as a novel medium-sized ornamental fish in the aquaria market.

We claim:

1. A construct comprising a Mlc3 promoter comprising the nucleotide sequence of SEQ ID NO. 1 and fused to a nucleotide sequence coding for a target protein, wherein the target protein is a luciferase protein.

2. A method for generating a transgenic fish, comprising the steps of:
   (iv) constructing the Mlc3 promoter of claim 1, ligated to a vector;
   (v) delivering the construct obtained in step (i) into embryos;
   (vi) identifying the transgenic fish.

3. A transgenic fish whose genome comprises the introduced construct of claim 1.

4. The transgenic fish of claim 3, wherein the fish is *Archocentrus* sp.

5. The transgenic fish of claim 3, wherein the fish is *A. nigrofasciatus*.

6. The transgenic fish of claim 3, which is a transgenic *A. nigrofasciatus* var. carrying Taiwan coral red fluorescent protein (TcRFP) driven by the Mlc3 promoter comprising the nucleotide sequence of SEQ ID NO. 1.

* * * * *

SEQUENCE LISTING

<160> NUMBER OF SEQ ID NOS: 34

<210> SEQ ID NO 1
<211> LENGTH: 6028
<212> TYPE: DNA
<213> ORGANISM: Oreochromis niloticus

<400> SEQUENCE: 1

```
ttctcttttt cttcctctgt gggaccatta gctcatctaa tccagtctttt tccatataag      60 gctcatgctg aaaaccaagc agcaacacaa tgccatctct cttttttaag ctccctgcca     120
gagctccttt atgacccaag gccagcttgg tagaaggagg tggtgaaggg ggaggtggct     180
actgtaccag agagtcttga gatcccagtc tccgcagagc aaacgcagcg taggagaaac     240
tcaacaccgc cagtgggaat gagagtaaaa atagagctca tctgtccagg aggggagtgg     300
tctccaaagg catgtgctcc actgtggttc acgcgctcct acaagtgtcc tccaacgtgt     360
ccgttctgat gctcagcagc tgattgcttt gtgttacata gacgatgaca agttaggcag     420
cctagcagca ctataagtga attatctaat cgtgtgtgct gtcacaatat aaatgcactg     480
accttttctt atagatttgt ctttccttcc ttttggatct actttagaga aaaaaattct     540
tctattttaa caatcgtata ttgttaaaat gtacttaacc aaaaggccaa aaaatgttta     600
tggaaatctg ctgtattctt acaactggtt gtacttaagg aggatcacag gcatgtagta     660
atgtgcaaaa gtcttgttcc atccctcatt tcttggtgtt taaggcaaaa acagagtttg     720
tacaattctg tcaagcttga aagtcaatat ttggtgtgac caccttttatt cttcagcaca     780 gtccgaactc tcttaggcag ctttcttgtt atttttttaa gttgtcttca ggaatagttc     840
tccaggcttc ttgaaggaca ttcagagctc ttctttggat gtttaaggac aggactttta     900
aatcttgtcc atctgcagtt gattttcag gcctgacatt tctgctttgg ccctcgactc     960
cagtttcctc aaatttttta attttgagga aactgcagtg catatgcata tgcacaccat    1020
atgcactgga gacctattgc tcaagaccaa ctgacggcaa ggaagtctcg ctcattgaa     1080 gcaaagtatt aacaatgact tttgcacagt actgtagctg gtatttatac ataattagca    1140
tgatattttt cattgataag tttatatttc attacacaca cgcgcacgca ggcatatata    1200
gtctccctca cctaaaccaa tctgccctga accttctaca acactcagtg ttaacacaca    1260
gggatcactg cttctaggct gttacccaca tggagtcaca tgtatgtgac agcagagatg    1320
agcatatatt taacctaaag catgaaaaaa aacaaaccca aacagatttc ttctatgaaa    1380
```

```
ttcacagctt tttaaatttt cagcaaattt tatatttgaa ataatagttt gtatcaacgg      1440
tactgtcaag ttgacaagta gactttccta aaaacaatac tataccagaa agactgtact      1500
gacaatacag gccctgaagc agaaaccaaa ccagcaataa acaaaccaat gaacatgact      1560
ataaaatgac ctgtgaacac cagagcctcc ttgttgtttg gacctatggg ttgttccaaa      1620
tagaaaaaga actgccagag gaactgaaaa acctaaatta aggatggaaa aaggatacaa      1680
gaagactggc gaccgacaga aagtcagtcg aagcacagct gcagcaataa tcgtgctaac      1740
cagcaactgg cctcctaaaa tgacaccatg ggcagtgcat tacttgcaca gtctagctct      1800
gagaaagctg gcgcttcaga tttggcacag ggtttataaa tggaaatggc tcacaacaca      1860
tagcataatg agatcctcta tggacggcac cctaagcgaa aaaacactgc tggctcttta      1920
acggaaaact ctatgatcga attttgctaa agaattccaa aagaaggctt atgaaagttg      1980
ggcgcatgcg gtccacagac gatgtccatg tgaaagattt tgggaagact ggtagattgt      2040
gtatatacca aaatactggt tgacaggatg gctcccagtc tgcagaggcc taacagaaca      2100
atgaggaaac tgccagaatc acactacaac ctgccctagt atgttgtcag acttgaatcc      2160
aataatcacc tttttaaaga gaaaagcaga gcagctgaaa tcaaagaata tcaggaaact      2220
gtcaatactg gcatccctcc aaacagacag caatgaataa attatttaaa aaacatgaaa      2280
gattcgtatg aatatgacag cctctaacca atcaaagact cctattatct ctattttccc      2340
tgtcttgtct ctatttctgc ctccttttct caatagtttt tagttctttg tgcctgtttc      2400
atgtagctgc tatgatgcta tattacctac ttgccaactg tttactttta gggtctggtc      2460
actatctcct accttcattt gtggttctgc cctgtgatac caaactaatt atgtaattcg      2520
aaccaagagt ctaattctat ccgaaaaact tacgttttta aaatttctg caaccctgaa      2580 ctgattggat tggatggacg gatggatgga tggatggatg gatggatgga tggatggatg      2640
gatggatgga tggatggatg gacagacaga cggatgtcaa acaacatata aagccaatgg      2700
gtaagtccat taagaaagat ctgtggtcac catgacacaa cttagagtcg ggaggatgga      2760
tggatggatt caattagatt tattatttgt cctttcagaa atttgtgcct cggggcgact      2820
gtcagacaaa taaccacaac aacaatatca cagttacaga gataaaagac atctgtttca      2880
tcccacatca taacaaatat cacctggatt tgttcaccag agttgtacaa ggtataaaca      2940
accttggggt gcgaggtcct cacaaagctg gtgtactgtc ttgactatga tgactgtgtg      3000
ttacgtccct gtgaatgtct cgcccctgtc ccatcactca tgactcccaa agctggcaca      3060
cactatgttg ttgctgacct cttactgccc atgtttacaa gcctactgag tttgttctta      3120
taaaccacgg agagtgaaaa caccagacaa taaaagaaaa agttaaaatg ctttctacag      3180
ataaacgatt aaaaagcatc tatgaatcta aactgttggg taataattgt atatgaggat      3240
tagttactat tacttacata agtaagaat aaccttgttg cttttgaaat tgtgatttgt       3300
aataggtggg ctataaataa cttgaaaaat aaaactgcac ttggagaatc agaggtaatg      3360
atatactata aagtcaataa aatgcaaagt gcagagaatt ttttccagtt ttttaaatta      3420
agtttgttac atcaaacaat gtatcaagaa attcatttat taagattaaa gcttattgca      3480
ttaaacaaag tttctttctg catcgctgtc agcaccatgg agagctctgc tgaagatgga      3540
aatgccaatg aaattgactt ttaaaaacgt catttattgt gctatgaatg tagttcttag      3600
taacataacc tacattatgt aagtttaact ttcctccagt gtatttgcct atttattaat      3660
ggacaaactg atcagttttt agtcagttga agccagcaaa tctgcacatt atgaatttat      3720
ttgttacttg tcctattctg agggtagcgc tgtgaggaca gatcttttta aggtctttag      3780
```

-continued

```
aattgttata aaacctgttg ttttcaggtt atctgccgct cagtgtcaat gcttttaaca    3840
catgcctgaa tggagtgaac ttttcaaatg attttccc ctcttctgtt atttaaccat     3900
aagaggagga gcagtgggc tgtttaaaaa taccaccctg taaatgagct cctcgcacct    3960
ggagccctcc tcaagtgagc ctcaaggaag ctgagttttc tgcatttca ctcaccagct    4020 gtacatctct ttccagagga gagaagtcta agtgtcaatg ctgccgaaag cattttggtt    4080
gaaattgtaa tgcattcaca gactctttga aatcttgcga ccgttctttc agccttctaa    4140
aaatagccct gtccccttct aaaggcctac tcccactgct ccgagggcgt acagctctcc    4200
tttccatttg ccctaagaaa gttaaagatg ttccaatgtg tcatctgatc tgcccattag    4260
catatgtgac atcacatgcc cggaataaat aagaggggtg ctttgaccat ggctaaggac    4320
cacactgtct tgggacttca gcttctcatc tcctccagct cctgctctcc aaaatggtgt    4380
gtacgaactt ctgttttgga ccttttgggt ggggcattgc tgatggagtt acctttttt     4440 ccttttaatt ggtttggata tcagctcgat aatgacccca aaactgagac ttttgctagt    4500
gaggcaaaat gaagactagc acccaggact agagtcttgg aatgcattca catgtatatg    4560
tttaatgtct aaaaaggctt atattctaat gcaaagaggc cgttttagag tttcagcatc    4620
catcatttgt tcagaaccct tttggacagt tacataagct ggatatactc attttgtttt    4680
tctttatttc tctgttttct gtgtgttgt gtatttgtta atgtgtgttt ttaaatgtga    4740
cagactgagt tcacaccgga ccagattgag ggtaagtgaa gaaaaggaaa aaagagatt    4800 ttgcctcata tgtgaaggca ccaacctctc agtcagtgtg ctggtaggca tttacgtcta    4860
acttttgcaa ctgtcacacg aaacaaactc tcagagtagc tccagactta cttagatgaa    4920
cttttaatct gattaaagtg ctagaaaagt ggaagcagag gatgaatagc gccatgccat    4980
gccattctac caacttctcc agctgtcggg aaagatttca gacatgtcta ttctcagctt    5040
gtcttgcgag tccccatggt ccttattcag aagggcatt aatccttagg tcagggttta    5100
agatgcagtg ctggtggcat cagcttacac aagaatctga atcaccccat acctttttg     5160 tttaactgcc gaaagacatg tcctctataa acatgcccta tgggatatat tagggtccc     5220 catttggaca tggatacttt tgtgtagtta aaactcttcc agttgtgtat cctagacttg    5280
caggcaaacc tttaacgagt tttcaatcag gcttatttgt ttagtgctgc ttctacacat    5340
tctggtacag ctatactata tgtctaacat taagttcctt tccaagtcac ggtgttaatt    5400
acggcccagt cagcattctt gggtttgact gcacggaggg ccatgtcgct atgtctctaa    5460
atggcctgcg tttctctgtc agggtgtatc agtttgctcg caatgttgct gtaaatgcaa    5520
gtggaggcag gaatgtagaa ggacggggtg ggtcgagtgt ggtggaaggg tacaactgct    5580
gttcagaagc cacacgaaca cattaatctg tcaaaaaggt cactttgagt tcctggtggg    5640
attcacagac atagccaacc attgtctggg cccccagttg gtgccttcct cttcacagct    5700
gtccctctca attagctgag aacaatgaca gaattatgtg gcttttactg tcttcctcta    5760
cattgtggca ctgtgcaact gacatagacg actagtagta acactgtaat agatagagta    5820
ggaaacccaa agccaaaggg gatggatcta acacagcaaa gaaaacatgg atgtcatgcc    5880
ataacaataa tatcaattat accatttgga tgggacaaag aaaaaactct ggcagacttt    5940
tttgttttaa tattttccat attgctgaag ccctaactat aagtcctgaa gcacttgtac    6000
tcaactttgt ttctctcctc ctggtcag                                       6028
```

<210> SEQ ID NO 2

```
<211> LENGTH: 28
<212> TYPE: DNA
<213> ORGANISM: Oreochromis niloticus

<400> SEQUENCE: 2
ttctcttttt cttcctctgt gggaccat                                    28

<210> SEQ ID NO 3
<211> LENGTH: 30
<212> TYPE: DNA
<213> ORGANISM: Oreochromis niloticus

<400> SEQUENCE: 3
ctgtcacatt taaaaacaca cattaacaaa                                  30

<210> SEQ ID NO 4
<211> LENGTH: 60
<212> TYPE: DNA
<213> ORGANISM: Oreochromis niloticus

<400> SEQUENCE: 4
ggggacaact ttgtatagaa aagttggcta gcttctcttt tcttcctct gtgggaccat   60

<210> SEQ ID NO 5
<211> LENGTH: 59
<212> TYPE: DNA
<213> ORGANISM: Oreochromis niloticus

<400> SEQUENCE: 5
ggggacaact ttgtatagaa aagttggcta gctactgaca atacaggccc tgaagcaga   59

<210> SEQ ID NO 6
<211> LENGTH: 60
<212> TYPE: DNA
<213> ORGANISM: Oreochromis niloticus

<400> SEQUENCE: 6
ggggacaact ttgtatagaa aagttggcta gcgcgactgt cagacaaata accacaacaa  60

<210> SEQ ID NO 7
<211> LENGTH: 56
<212> TYPE: DNA
<213> ORGANISM: Oreochromis niloticus

<400> SEQUENCE: 7
ggggactgct tttttgtaca aacttgctgt cacatttaaa aacacacatt aacaaa      56

<210> SEQ ID NO 8
<211> LENGTH: 30
<212> TYPE: DNA
<213> ORGANISM: Oreochromis niloticus

<400> SEQUENCE: 8
caacttttct atacaaagtt gatagcttgg                                  30

<210> SEQ ID NO 9
<211> LENGTH: 30
<212> TYPE: DNA
<213> ORGANISM: Oreochromis niloticus

<400> SEQUENCE: 9
caagtttgta caaaaaagca ggcttagcca                                  30
```

<210> SEQ ID NO 10
<211> LENGTH: 46
<212> TYPE: DNA
<213> ORGANISM: Oreochromis niloticus

<400> SEQUENCE: 10
ggggacaact tgtatagaa aagttgatgc tgtgaagtat tctcta          46

<210> SEQ ID NO 11
<211> LENGTH: 46
<212> TYPE: DNA
<213> ORGANISM: Oreochromis niloticus

<400> SEQUENCE: 11
ggggactgct tttttgtaca aacttggtag tgtcctgtac ttgagg          46

<210> SEQ ID NO 12
<211> LENGTH: 27
<212> TYPE: DNA
<213> ORGANISM: Oreochromis niloticus

<400> SEQUENCE: 12
cggtcgacag gcagcctagc agcacta          27

<210> SEQ ID NO 13
<211> LENGTH: 28
<212> TYPE: DNA
<213> ORGANISM: Oreochromis niloticus

<400> SEQUENCE: 13
cggtcgacag tttgtacaat tctgtcaa          28

<210> SEQ ID NO 14
<211> LENGTH: 26
<212> TYPE: DNA
<213> ORGANISM: Oreochromis niloticus

<400> SEQUENCE: 14
cggtcgacta gctggtattt atacat          26

<210> SEQ ID NO 15
<211> LENGTH: 28
<212> TYPE: DNA
<213> ORGANISM: Oreochromis niloticus

<400> SEQUENCE: 15
cggtcgacaa ttcgaaccaa gagtctaa          28

<210> SEQ ID NO 16
<211> LENGTH: 27
<212> TYPE: DNA
<213> ORGANISM: Oreochromis niloticus

<400> SEQUENCE: 16
cggtcgactt cttataaacc acggaga          27

<210> SEQ ID NO 17
<211> LENGTH: 22
<212> TYPE: DNA
<213> ORGANISM: Oreochromis niloticus

<400> SEQUENCE: 17
gttgggtaat aattgtatat ga          22

```
<210> SEQ ID NO 18
<211> LENGTH: 28
<212> TYPE: DNA
<213> ORGANISM: Oreochromis niloticus

<400> SEQUENCE: 18
cggtcgactt gttgcttttg aaattgtg                                28

<210> SEQ ID NO 19
<211> LENGTH: 22
<212> TYPE: DNA
<213> ORGANISM: Oreochromis niloticus

<400> SEQUENCE: 19
aaataacttg aaaaataaaa ct                                      22

<210> SEQ ID NO 20
<211> LENGTH: 28
<212> TYPE: DNA
<213> ORGANISM: Oreochromis niloticus

<400> SEQUENCE: 20
cggtcgacct gcacttggag aatcagag                                28

<210> SEQ ID NO 21
<211> LENGTH: 20
<212> TYPE: DNA
<213> ORGANISM: Oreochromis niloticus

<400> SEQUENCE: 21
aaattaagtt tgttacatca                                         20

<210> SEQ ID NO 22
<211> LENGTH: 19
<212> TYPE: DNA
<213> ORGANISM: Oreochromis niloticus

<400> SEQUENCE: 22
ccatggagag ctctgctga                                          19

<210> SEQ ID NO 23
<211> LENGTH: 26
<212> TYPE: DNA
<213> ORGANISM: Oreochromis niloticus

<400> SEQUENCE: 23
cggtcgactt atgtaagttt aacttt                                  26

<210> SEQ ID NO 24
<211> LENGTH: 27
<212> TYPE: DNA
<213> ORGANISM: Oreochromis niloticus

<400> SEQUENCE: 24
cggtcgacgc cgctcagtgt caatgct                                 27

<210> SEQ ID NO 25
<211> LENGTH: 27
<212> TYPE: DNA
<213> ORGANISM: Oreochromis niloticus

<400> SEQUENCE: 25
cggtcgacag aggagagaag tctaagt                                 27
```

```
<210> SEQ ID NO 26
<211> LENGTH: 26
<212> TYPE: DNA
<213> ORGANISM: Oreochromis niloticus

<400> SEQUENCE: 26
cggtcgactt ctaaaaatag ccctgt                                          26

<210> SEQ ID NO 27
<211> LENGTH: 27
<212> TYPE: DNA
<213> ORGANISM: Oreochromis niloticus

<400> SEQUENCE: 27
cggtcgactg tccccttcta aaggcct                                         27

<210> SEQ ID NO 28
<211> LENGTH: 26
<212> TYPE: DNA
<213> ORGANISM: Oreochromis niloticus

<400> SEQUENCE: 28
tagtgctgct aggctgccta acttgt                                          26

<210> SEQ ID NO 29
<211> LENGTH: 24
<212> TYPE: DNA
<213> ORGANISM: Oreochromis niloticus

<400> SEQUENCE: 29
agccatggtc aaagcacccc tctt                                            24

<210> SEQ ID NO 30
<211> LENGTH: 24
<212> TYPE: DNA
<213> ORGANISM: Oreochromis niloticus

<400> SEQUENCE: 30
tttggagagc aggagctgga ggag                                            24

<210> SEQ ID NO 31
<211> LENGTH: 36
<212> TYPE: DNA
<213> ORGANISM: Oreochromis niloticus

<400> SEQUENCE: 31
aggcgtcgac ggatccttct cttttcttc ctctgt                                36

<210> SEQ ID NO 32
<211> LENGTH: 28
<212> TYPE: DNA
<213> ORGANISM: Oreochromis niloticus

<400> SEQUENCE: 32
catctagact gtcacattta aaaacaca                                        28

<210> SEQ ID NO 33
<211> LENGTH: 29
<212> TYPE: DNA
<213> ORGANISM: Oreochromis niloticus

<400> SEQUENCE: 33
```

-continued

```
ggtctagaat ggctctgtca aagcacggt                                        29
```

<210> SEQ ID NO 34
<211> LENGTH: 27
<212> TYPE: DNA
<213> ORGANISM: Oreochromis niloticus

<400> SEQUENCE: 34

```
gtagatcttt atccgggcaa tgcggat                                          27
```